(12) United States Patent
Ross (10) Patent No.: US 8,226,825 B2
(45) Date of Patent: Jul. 24, 2012

(54) RECIRCULATING TEMPERATURE WAVE FOCUSING CHROMATOGRAPHY

(75) Inventor: David J. Ross, Silver Spring, MD (US)

(73) Assignee: The United States of America, as represented by the Sectretary of Commerce, The National Institute of Standards and Technology, Washington, DC (US)

(*) Notice: Subject to any disclaimer, the term of this patent is extended or adjusted under 35 U.S.C. 154(b) by 458 days.

(21) Appl. No.: 12/506,370

(22) Filed: Jul. 21, 2009

(65) Prior Publication Data

US 2009/0320560 A1    Dec. 31, 2009

Related U.S. Application Data

(60) Provisional application No. 61/168,020, filed on Apr. 9, 2009.

(51) Int. Cl.
*B01D 15/08* (2006.01)

(52) U.S. Cl. ............ 210/198.2; 210/656; 210/143; 95/86; 95/87; 96/102; 96/103; 96/104

(58) Field of Classification Search .......... 210/656, 210/659, 96.1, 143, 198.2; 95/82, 86, 87; 96/101, 102, 103, 104
See application file for complete search history.

(56) References Cited

U.S. PATENT DOCUMENTS

| | | | |
|---|---|---|---|
| 3,062,039 A | | 11/1962 | Ayers |
| 3,156,548 A | * | 11/1964 | Perry .............................. 96/104 |
| 3,206,968 A | * | 9/1965 | Leggoe et al. ............... 73/23.35 |
| 3,557,532 A | | 1/1971 | Broerman |
| 3,698,156 A | * | 10/1972 | Dirian .............................. 95/86 |
| 4,154,583 A | * | 5/1979 | Favre et al. ...................... 95/86 |
| 4,923,486 A | | 5/1990 | Rubey |
| 5,028,243 A | | 7/1991 | Rubey |
| 5,071,547 A | * | 12/1991 | Cazer et al. ................. 210/198.2 |
| 5,114,439 A | | 5/1992 | Yost et al. |
| 5,135,549 A | * | 8/1992 | Phillips et al. ...................... 95/8 |
| 5,152,176 A | * | 10/1992 | Bryselbout et al. .......... 73/23.41 |
| 5,215,556 A | | 6/1993 | Hiller et al. |

(Continued)

FOREIGN PATENT DOCUMENTS

WO    2006127490 A1    11/2006

(Continued)

OTHER PUBLICATIONS

V. G. Berezkin, T Yu Chernysheva, V. V. Buzayev, M. A. Koshevnik; "Temperature Gradients in Gas Chromatography"; Journal of Chromatography; 1986; 373; 21-44.

(Continued)

*Primary Examiner* — Ernest G Therkorn
(74) *Attorney, Agent, or Firm* — Rankin, Hill & Clark LLP (57) ABSTRACT

Systems and methods for performing chromatography separations or analyses are disclosed. The methods are based upon an equilibrium gradient focusing mode in contrast to conventional transient migration-based modes. By matching the migration speed of one or more analyte(s) of interest to the wave speed of a thermal gradient induced to travel along a region in which chromatographic partitioning occurs, significant improvements in detection limits are achieved. In particular, a temperature gradient focusing strategy is described in which analyte(s) of interest are circulated around a continuous chromatography system in order to focus the analyte (s). Also described are various devices and systems that can be used in the methods described herein.

8 Claims, 8 Drawing Sheets

U.S. PATENT DOCUMENTS

| | | | | |
|---|---|---|---|---|
| 5,492,555 | A | * | 2/1996 | Strunk et al. ............... 95/86 |
| 5,547,497 | A | * | 8/1996 | Klemp et al. ............... 96/104 |
| 6,153,438 | A | | 11/2000 | Blumberg et al. |
| 6,497,138 | B1 | * | 12/2002 | Abdel-Rahman et al. ... 73/23.42 |
| 6,530,260 | B1 | | 3/2003 | Mustacich et al. |
| 2004/0206626 | A1 | | 10/2004 | Ross et al. |
| 2005/0145495 | A1 | | 7/2005 | Ross et al. |
| 2005/0258040 | A1 | | 11/2005 | Ross et al. |
| 2005/0274174 | A1 | | 12/2005 | Tai et al. |

FOREIGN PATENT DOCUMENTS

WO           2008086357 A2     7/2008

OTHER PUBLICATIONS

L. M. Blumberg; "Limits of Resolution and Speed of Analysis in Linear Chromatography with and without Focusing"; Chromatographia; Dec. 1994; vol. 39, No. 11/12; 719-728.

J. Luong, R. Gras, R. Mustacich, H. Cortes; "Low Thermal Mass Gas Chromatography: Principles and Applications"; Journal of Chromatographic Science; May/Jun. 2006; vol. 44; 253-261.

W. Rubey; "A Different Operational Mode for Addressing the General Elution Problem in Rapid Analysis Gas Chromatography"; Journal of High Resolution Chromatography; Aug. 1991; vol. 14; 542-548.

W. Rubey; "Operational Theory and Instrumental Implementation of the Thermal Gradient Programmed Gas Chromatography (TGPGC) Mode of Analysis"; Journal of High Resolution Chromatography; Dec. 1992; vol. 15; 795-799.

A. P. Tudge; "Studies in Chromatographic Transport, III Chromathermography"; Canadian Journal of Physics; 1962; vol. 40; 557-572.

A. A. Zhukhovitsky, N. M. Turkeltaub, "Application of the Thermal Factor in Gas Chromatography"; 1967; vol. 116; No. 6; 986-989.

C.M.A. Badger, J.A. Harris, K.F. Scott, M.J. Walker, C.S.G. Phillips; "Heater-Displacement Chromatography"; Journal of Chromatography, 126 (1976) 11-18.

L.M. Blumberg; "Focusing Cannot Enhance Resolution or Speed Limit of a GC Column"; Journal of Chromatographic Science; 1997; 35; 451-454.

Graham T. Eyres, Sylvia Urban, Paul D. Morrison, Jean-Pierre Dufour, Philip J. Marriott; "Method for Small-Molecule Discovery Based on Microsale-Preparative Multidimensional Gas Chromatography Isolation with Nuclear Magnetic Resonance Spectroscopy"; Analytical Chemistry; Published on Web Jul. 23, 2008.

Gad Frishman, Aviv Amirav; "Fast GC-PFPD System for Field Analysis of Chemical Warfare Agents"; Field Analytical Chemistry and Technology; 2000; 4(4):170-194.

Mark E. Hail, Richard A. Yost; "Compact Gas Chromatograph Probe for Gas Chromatography/Mass Spectrometry Utilizing Resistively Heated Aluminum-Clad Capillary Columns"; Analytical Chemistry; 1989; 61; 2410-2416.

Anders Holm, Paal Molander, Elsa Lundanes, Tyge Greibrokk; "Novel column oven concept for cold spot large volume sample enrichment in high throughput temperature gradient capillary liquid chromatography"; Journal of Separation Science; 2003; 26; 1147-1153.

Gordon R. Lambertus, Cory S. Fix, Shaelah M. Reidy, Ranaan A. Miller, David Wheeler, Erkinjon Nazarov, Richard Sacks; "Silicon Microfabricated Column with Microfabricated Differential Mobility Spectrometer for GC Analysis of Volatile Organic Compounds"; Analytical Chemistry; Dec. 1, 2005; vol. 77; No. 23.

Philip J. Marriott, Russell M. Kinghorn; "Longitudinally Modulated Cryogenic System. A Generally Applicable Approach to Solute Trapping and Mobilization in Gas Chromatography"; Analytical Chemistry; 1997; 69(13); 2582-2588.

Marco Mazzotti, Giuseppe Storti, Massimo Morbidelli; "Supercritical fluid simulated moving bed chromatography"; Journal of Chromatography A; 786 (1997) 309-320.

Cristiano Migliorini, Michael Wendlinger, Marco Mazzotti; "Temperature Gradient Operation of a Simulated Moving Bed Unit"; Industrial Engineering Chemistry Research; 2001; 40; 2606-2617.

P. Molander, K. Haugland, D.R. Hegna, E. Ommundsen, E. Lundanes, T. Greibrokk; "Determination of low levels of an antioxidant in polyolefins by large-volume injection temperature-programmed packed capillary liquid chromatography"; Journal of Chromatography A.; 864 (1999); 103-109.

Leslie K. Moore and Robert E. Synovec; "Axial Thermal Gradient Microbore Liquid Chromatography by Flow Programming"; Analytical Chemistry; 1993; 65; 2663-2670.

R. Wayne Online, Donald D. DeFord; "Chromatherapy, the Application of Moving Thermal Gradients to Gas Liquid Partition Chromatography"; Analytical Chemistry; Feb. 1963; vol. 35; No. 2.; 227-234.

H. Lakhiari, T. Okano, N. Nurdin, C. Luthi, P. Descouts, D. Muller, J. Jozefonvicz; "Temperature-responsive size-exclusion chromatography using poly (N-isopropylacrylamide) grafted silica"; Abstract only; ScienceDirect—Biochimica et Biophysica Acta (BBA)—General Subjects; Available online Apr. 30, 1998.

Wayne A. Rubey; "An instrumentation assembly for studying operational behavior of thermal gradient programmed gas chromatography"; Review of Scientific Instruments; Sep. 1994; 65 (9); 2802-2807.

Stephen C. Terry, John H. Jerman, James B. Angell; "A Gas Chromatographic Air Analyzer Fabricated on a Silicon Wafer"; IEEE Transactions on Electron Devices, Dec. 1979; vol. Ed-26; No. 12; 1880-1886.

Feng Xu, Weena Guan, Guiyan Yao, Yafeng Guan; "Fast temperature programming on a stainless-steel narrow-bore capillary column by direct resistive heating for fast gas chromatography"; Journal of Chromatography A; 1186; (2008) 183-188.

Hong Zhao, Lihua Yu, Jian Zhang, Yafeng Guan; "Characteristics of TGPGC on Short Micro Packed Capillary Column"; Analytical Sciences; Jan. 2002, vol. 18; 93-95.

A.A. Zhukhovitsky, N. M. Turkeltaub; "Application of the Thermal Factor in Gas Chromatography"; http://firstsearch.oclc.org; Dec. 20, 2005; 657-660.

Thomas Birger Jensen; "Gradient SMB Chromatography"; ISBN 90-6464-953-7; Jun. 10, 2003; 1-126.

V. Jain, J. B. Phillips; "Focusing cannot enhance resolution or speed limit of a GC column—Response"; Journal of Chromatographic Science; Sep. 1997; vol. 35; (9); 454-456.

V. Jain, J. Phillips; "High-Speed Gas Chromatography Using Simultaneous Temperature Gradients in Both Time and Distance Along Narrow-Bore Capillary Columns"; Journal of Chromatographic Science; Nov. 1995; vol. 33; (11); 601-605.

J. Phillips, V. Jain; "On-Column Temperature Programming in Gas Chromatography Using Temperature Gradients Along the Capillary Columns"; Journal of Chromatographic Science; Oct. 1995; vol. 33; (10) 541-550.

V. Jain, J. Phillips; Fast Temperature Programming on Fused-Silica Open-Tubular Capillary Columns by Direct Resistive Heating; Journal of Chromatographic Science; Jan. 1995; vol. 33; (1); 55-59.

L. M. Blumberg; "Variance of a zone migrating in a linear medium II. Time-varying non-uniform medium"; Journal of Chromatography; 1993; 637; 119-128.

B. A. Rudenko; "Effect of Linear-Gradient-Loaded Columns on Column Efficiency in Gas-Liquid Chromatography"; Journal of Analytical Chemistry of the USSR; 1981; vol. 36; Issue 11; 1569-1578.

H. A. Hancock, A. Cataldi; "New Temperature Programming Technique for Gas Chromatography"; Journal of Gas Chromatography; 1967; vol. 5; Issue 8; 406-408.

E. U. Ehrmann, H. P. Dharmasena, K. Carney, E. B. Overton; "Novel Column Heater for Fast Capillary Gas Chromatography"; Journal of Chromatographic Science; 1996; vol. 34; Issue 12; 533-539.

M. Coudert, J. M. Vergnaud; "Retention in Gas Chromatography Obtained With a Longitudinal Temperature Gradient With a Constant Growth Rate"; Journal of Chromatography; 1971; vol. 54; Issue 1; 1-8.

P. E. Duarte, B. J. McCoy; "Stationary Spatial Temperature Gradient in Gas Chromatography"; Separation Science and Technology; 1982; vol. 17; Issue 7; 879-896.

* cited by examiner

FIG. 11

RECIRCULATING TEMPERATURE WAVE FOCUSING CHROMATOGRAPHY

CROSS REFERENCES TO RELATED APPLICATIONS

This application claims priority from U.S. provisional application Ser. No. 61/168,020 filed on Apr. 4, 2009.

STATEMENT AS TO RIGHTS TO INVENTION(S) MADE UNDER FEDERALLY-SPONSORED RESEARCH AND DEVELOPMENT

The U.S. Government, through the National Institute of Standards and Technology, is the owner of this invention.

FIELD OF THE INVENTION

The present invention relates to systems and methods for performing chromatography in an equilibrium gradient focusing mode rather than a transient, migration-based mode as conventionally known. In particular, the present invention utilizes temperature gradient focusing and a recirculating temperature wave for various chromatography applications.

BACKGROUND OF THE INVENTION

Most commonly used techniques for analytical separations (such as for example gas chromatography, periodically referred to herein as "GC"; liquid chromatography, periodically referred to herein as "LC"; and capillary electrophoresis, periodically referred to herein as "CE"; etc.) begin with the injection of a plug of a multi-component sample at the beginning of a separation column and proceed with the migration of the sample plug along the column. Separation occurs as each analyte in the sample migrates with a different speed and so can be individually detected at the end of the column. There are two primary drawbacks to this type of separation. First, the injected sample plug must be very narrow to achieve good resolution of the migrating analytes. Second, the widths of the individual analyte bands increase and their amplitudes decrease as they migrate along the column. Consequently, it can be difficult to achieve both high resolution and low concentration detection limits in the same analysis. For GC in particular, and to a lesser extent for LC, a number of methods have been developed for the injection of a large amount of sample to improve detection limits followed by compression of the sample plug into a narrow starting band required for high resolution. There are significant disadvantages and limitations to these methods however. The most common problems are thermal degradation of analytes due to the high temperature of the injection chamber and biasing of either high or low affinity analytes.

A different approach to analytical separations is the use of an equilibrium gradient focusing method such as isoelectric focusing (IEF). With this type of approach, a gradient (in pH, electric field, density, temperature, etc.) is formed along the length of the separation column and different analytes are separated as they are made to focus or accumulate at different positions along the gradient. A major advantage of this strategy, referred to as "analyte focusing," is that it combines the concentration and separation of analytes into one step. As a result, peaks become narrower and more concentrated as the separation progresses. A second important advantage is that the width of the injected sample plug need not be carefully defined, since the analytes will move toward and be focused at their respective positions regardless of how they were introduced into the column. Consequently, it is relatively easy to achieve both high resolution and low detection limits.

To achieve analyte focusing at a stationary position requires either a single force that changes direction at the focusing position or a combination of two counteracting forces arranged so that the sum of the forces changes direction at the focusing position. However, in LC and GC, there is only one force, the flow of mobile phase through the column. The flow cannot be made to change direction in the middle of the column. And so, it appears that it would not be possible to achieve the advantages of a focusing mode separation in LC or GC.

Regardless, it would be desirable to provide a method and related system for performing chromatography in an equilibrium gradient focusing mode. More specifically, it would be desirable to provide a technique and related system whereby analyte focusing could be performed in a chromatography process such as gas chromatography or liquid chromatography.

Attempts have been made by prior artisans to perform a chromatographic process based upon an equilibrium gradient focusing mode as opposed to a time-based migration mode, which nearly all conventional chromatography processes employ. In the 1950s, as GC was being developed, an equilibrium gradient focusing mode of GC was investigated— primarily by a Russian group led by Zhukhovitskii and Turkel'taub. Their results demonstrated the validity of the idea but were limited ultimately by the slow thermal equilibrium of the large-bore GC columns used at the time. The advent of microbore GC (and LC) columns in the 1970s would seem to have been an opportunity to try the idea again, but by then most research groups seem to have been wedded to the conventional approaches of isothermal and temperature-programmed (with a temperature gradient in time only) chromatography. It was not until the 1990s that the approach was tried with capillary columns. Even then, as far as is known, it was only pursued by two groups, and their focus was primarily on using the technique to increase the peak capacity per unit time of GC separations. Specifically, a group led by Wayne A. Rubey investigated the use of both spatial and temporal temperature gradients in capillary GC applications. Descriptions of Rubey's work in this regard are noted in "An Instrumentation Assembly for Studying Gradient Programmed Gas Chromatography," *Rev. Sci. Instrum.*, 65 (9), September 1994, p. 2802-2807; U.S. Pat. No. 4,923,486 to Rubey; and International Patent Publication No. WO 2006/127490 to Rubey et al. Another group, Phillips and Jain published two papers on this subject in 1995, "On-Column Temperature Programming in Gas-Chromatography Using Temperature-Gradients Along the Capillary Column," *Journal of Chromatographic Science*, 33 (10), October 1995, p. 541-550; and "High-Speed Gas-Chromatography Using Simultaneous Temperature-Gradients In Both Time And Distance Along Narrow-Bore Capillary Columns," *Journal of Chromatographic Science*, 33 (11), November 1995, p. 601-605.

The conclusions stated in the work by Phillips and Jain were disputed by a leading researcher in the field. In 1997, LM Blumberg published "Focusing Cannot Enhance Resolution or Speed Limit of a GC Column," *J. Chromatographic Science*, Vol. 35, September 1997, p. 451-454. In that letter, Blumberg disputed the previous claims of Phillips and Jain, and also the previous work by Rubey. After it was theoretically proven that the earlier claims by these two groups were essentially impossible, publication on the subject essentially stopped.

SUMMARY OF THE INVENTION

The difficulties and drawbacks associated with previous systems and approaches are overcome in the present system and method for a chromatography system using an equilibrium gradient focusing mode.

In one aspect, the present invention provides a chromatography system for separating one or more analytes from a mixture. The system comprises a plurality of chromatography columns, each chromatography column defining inlet and outlet ends. The system also comprises a system for generating a retention gradient in both time and distance along at least a portion of the length of at least one of the chromatography columns. And, the system also comprises at least one selection valve in flow communication with the inlet ends and the outlet ends of the plurality of chromatography columns. A mobile phase can be directed to flow sequentially through each of the chromatography columns. The selection valve can be switched to control the order in which the mobile phase flows through each of the chromatography columns.

In another aspect, the present invention provides a method for analyzing one or more analyte(s) from a mixture. The method comprises providing a chromatography system including a plurality of chromatography columns. The method also comprises directing a mobile phase to flow sequentially through each of the chromatography columns. The method further comprises introducing one or more analyte(s) into the chromatography columns. The method additionally comprises periodically switching the order in which the mobile phase flows through the chromatography columns. And, the method includes generating a retention gradient in both time and distance along at least a portion of the length of at least one of the chromatography columns such that the retention gradient is alternately increased and decreased in time and in a manner that is coordinated with the switching of the order in which the mobile phase flows through the chromatography columns. One or more analyte(s) are focused into chromatographic peaks and are circulated repeatedly through each of the chromatography columns.

As will be realized, the invention is capable of other and different embodiments and its several details are capable of modifications in various respects, all without departing from the invention. Accordingly, the drawings and description are to be regarded as illustrative and not restrictive.

DETAILED DESCRIPTION OF THE EMBODIMENTS

The present invention utilizes temperature gradient focusing (TGF) for a wide array of chromatography applications. The invention is based upon a discovery that by recirculating a moving temperature wave through a system preferably comprising two or more chromatography columns, analytes accumulate at select locations on the temperature wave. Thus, analyte peaks become narrower and more intense as the temperature wave is circulated about the system. The resulting focusing of analyte peaks enables higher resolution and lower detection limits for the system.

As described herein, the present invention provides a unique strategy for enabling equilibrium gradient focusing in chromatographic operations, and preferably, for gas chromatography and liquid chromatography processes. Before turning attention to the present invention and its various embodiments, it is instructive to first consider chromatography techniques in general.

Chromatography Techniques

Traditional chromatography is a separation process based on partitioning of sample mixture components or "analytes" between a "stationary phase" and a "mobile phase." The stationary phase is provided by the surface of solid materials which can comprise many different materials in the form of particles or passageway surfaces of cellulose, silica gel, coated silica gel, polymer beads, and polysaccharides, for example. These materials can be supported on solid surfaces such as on glass plates or packed in a column. The mobile phase can be a liquid or a gas such as in gas chromatography. The term "column" as used herein refers to any enclosure or housing adapted for use in a chromatography process and suitable for retaining all or part of a stationary phase and enabling a mobile phase to contact the stationary phase. Typically, such columns are in the form of conduits, tubes, or other structures having a relatively large ratio of flow length to flow cross section. Preferably, the column defines a cylindrically shaped hollow interior with a volume that can be characterized by its flow length and internal radius. For various GC chromatography applications, a capillary member can receive a coating of a stationary phase material on its inner capillary wall. This practice is employed in the preferred embodiments described herein.

The separation principles in any chromatography process are generally the same regardless of the materials used, the form of the materials, or the apparatus used. The analytes in a sample mixture have different respective degrees of solubility in the stationary phase and in the mobile phase. Therefore, as the mobile phase flows over, through, or alongside the stationary phase, there is an equilibrium in which the analytes are partitioned between the stationary phase and the mobile phase. Analytes are said to be strongly retained or to have a high retention if they are predominantly partitioned into the stationary phase. Analytes are said to be weakly retained or to have a low retention if they are predominantly partitioned into the mobile phase.

A separation of a mixture of analytes occurs because the different analytes have different affinities for the stationary phase and/or solubilities in the mobile phase, and therefore will be retained to different degrees. Therefore, the different analytes pass through the column at different rates.

Figure 1:
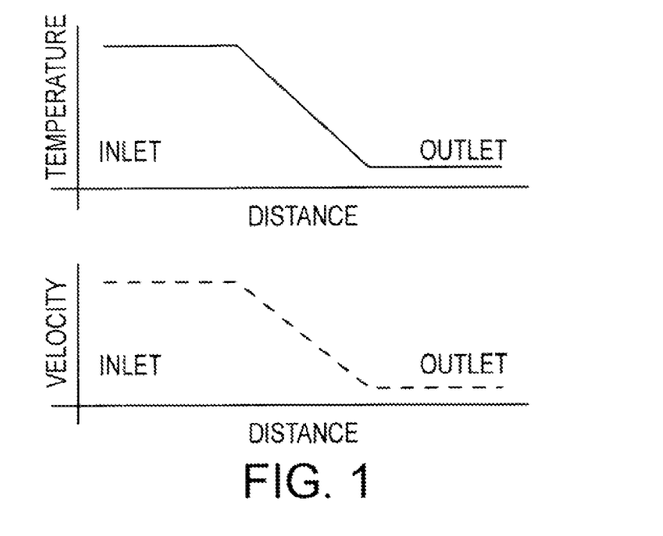
FIG. 1 includes representative plots of temperature versus distance and velocity versus distance in a typical chromatography column.
Figure 2:
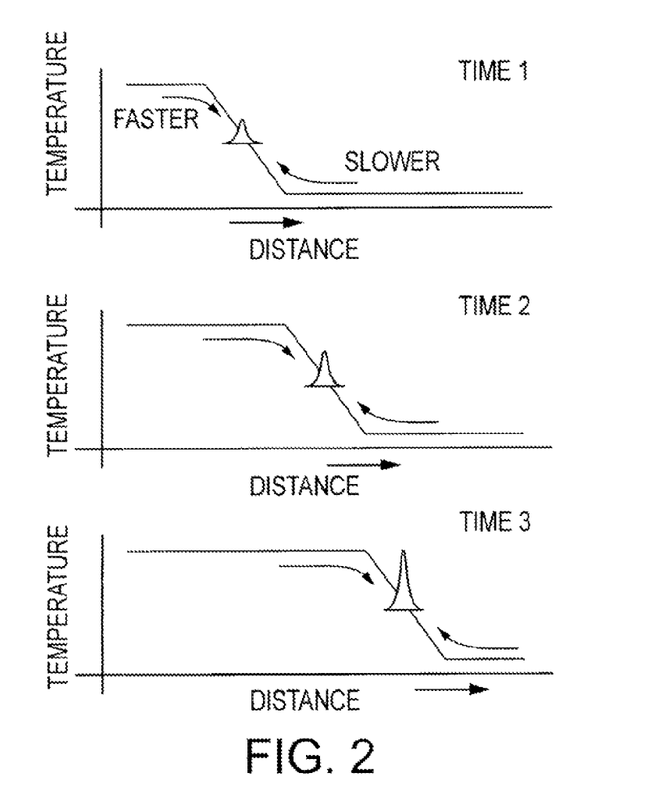
FIG. 2 includes representative plots of temperature versus distance at three different times for a chromatography column in which a temperature gradient is moved along the column.

The present invention may be better understood and appreciated by considering the following. A chromatography column with a temperature profile applied along its length is shown in FIG. 1, with the inlet end of the column at a high temperature, the outlet end at a low temperature, and a temperature gradient zone in the middle. Since the retention of an analyte to the stationary phase in the column will depend on the local temperature, the velocity of the analyte moving through the column will then have a profile similar to the temperature—high velocity at the inlet and lower velocity at the outlet. If the temperature gradient is then made to move along the column like a wave as shown in FIG. 2, the velocities of the mobile phase and of the temperature wave can be set or otherwise adjusted to one another so that analyte at the high temperature end will migrate faster than the wave, and analyte at the low temperature end will move slower than the wave. All of the analyte in the column will then be swept up and focused at the (moving) position at which the temperature is such that the velocity of the analyte is equal to the velocity of the temperature wave. Different analytes, with different retention versus temperature characteristics, will be focused at different positions on the wave, and thereby separated.

Preferred Embodiments

A primary goal of the present invention is to utilize a moving temperature gradient to improve the detection limits of a separation. Although use of a moving temperature gradient may also improve peak capacity, the present invention strives to improve the detection limits of a separation. Because of the focusing effect, the width and resolution of the analyte peaks at the end of a separation are unaffected by the width of the initial injection. So, unlike in a conventional GC or LC separation, a very long plug of sample can be injected. It is even possible to use a series of injections with each one adding to the accumulation of dilute analytes until a quantifiable amount is present. Because the analytes are focused on a moving temperature wave rather than at stationary locations, the primary limitation to the length or number of injections that can be used to accumulate analyte for a single separation is generally dictated by the length of the column. Therefore, in order to achieve the maximum possible gains in detection limits, the present invention can utilize multiple columns and preferably uses two identical columns, and alternates the temperature wave and focused analytes between the columns to realize an effectively infinite column length. The focused peak pattern can thus be maintained and recirculated around the loop formed by the two or more columns. The recirculation of the peak pattern around the column loop on a moving temperature gradient allows for several manipulations that are not possible with prior art methods of chromatography. First, it is possible to sum an unlimited number of sequential injections to achieve very low detection limits. Second, it is possible to "zoom in on" specific regions of a chromatogram, to enhance the resolution without stopping or rerunning the analysis. Third, it is possible to "cut out" or remove from the pattern, high concentration analyte peaks that would otherwise interfere with the detection of trace analytes of interest. Fourth, it is possible to directly measure analyte retention versus temperature. These and other aspects of the present invention are described in greater detail herein.

An analytical separation in accordance with the present invention preferably comprises two steps: an injection or accumulation step, and an analysis or identification step. During the injection step, one or more injections of sample is made into the column loop. The analyte peaks are summed on the moving gradient and high concentration interferents are "cut out" of the peak pattern, with the peak cutting being done possibly as often as every injection cycle. During the injection step, a non-destructive detector is preferably used to monitor the accumulation of analytes in the focused peaks. For LC, a standard low-volume UV absorbance cell can be used. For GC, the choice of non-destructive detector may for example be a thermal conductivity detector (TCD) or a photoionization detector (PID). For the examples described herein, a TCD was used because of its relatively low cost and simplicity. For the identification step, one or more valves can be switched to elute the peaks off the column loop to a more selective and sensitive (and typically destructive) detector such as a flame ionization detector or mass spectrometer. This approach is also quite flexible. For example, high concentration analytes can be "cut out" of the focused peak pattern after each injection as the peak pattern passes between columns on the loop so that they do not interfere with the detection of trace analytes. Furthermore, because the sample is preferably injected directly on column, without the use of a split valve or other potential source of bias (which may otherwise result in a loss or partial loss of some analytes), trace analyses with this technique can be much more reliably quantitative than with conventional large volume injection techniques.

A preferred embodiment of the invention comprises two or more chromatography columns arranged in a loop so that the mobile phase and analytes pass through each column of the loop in turn. The preferred embodiment may further comprise components and/or systems to apply a retention gradient in both time and distance along at least a portion of the length of one or more of the columns. Preferably, the system for generating a retention gradient includes one or more components for generating a moving temperature gradient (a gradient in both time and distance along the column) to at least one of the columns in the loop. Representative examples of such strategies for applying a moving temperature gradient are described in the prior art. Examples include: Phillips and Jain, *Journal of Chromatographic Science*, vol. 33, p 541 (1995); Jain and Phillips, *Journal of Chromatographic Science*, vol. 33, p 601 (1995); Rubey, *Journal of High Resolution Chromatography*, vol. 15, p 795 (1992); Rubey, *Review of Scientific Instruments*, vol. 65, p 2802 (1994); U.S. Pat. No. 4,923,486; U.S. Pat. No. 5,028,243; and WIPO Patent No. WO/2006/127490; Zhoa et al. *Analytical Sciences*, vol. 18, pp. 93-95 (2002). Several of these examples use heat exchanger arrangements to form temperature gradients. In these arrangements, the column is typically contained in a tube, groove, or other conduit along with a long heater. Examples of heaters used in this way include heating wires, conducting paint or film applied to the chromatography column, metal (stainless steel or nickel, typically) tubing with the column inside, or the column itself if the column is made of a conducting material. Heat is applied by passing electric current through the heater, and a heat exchange fluid (liquid or gas) is caused to flow along the conduit. As the fluid flows along the heater inside the conduit, the fluid is heated, and a temperature gradient is thus formed along the conduit (and therefore along the column) with the end at which the fluid enters the conduit being cooler than the end at which the fluid leaves the conduit.

The preferred embodiment of the invention may further comprise one or more valves to control the order in which the mobile phase and analytes pass through the columns forming the loop. In the examples described below, for example, there are two columns, A and B, that form the loop, and a 10 port, two-position, selection valve that is used to control the order of the columns in the loop. With the selection valve in the first position, the mobile phase flows first through column A and then through column B. With the selection valve in the second position, the mobile phase flows first through column B and then through column A.

Figure 3:
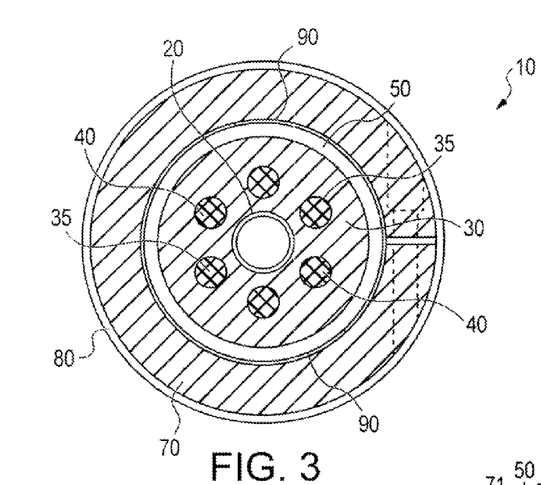
FIG. 3 is a schematic cross sectional view of a preferred embodiment chromatography apparatus taken along a plane generally transverse to a longitudinal axis of the apparatus.
Figure 4:
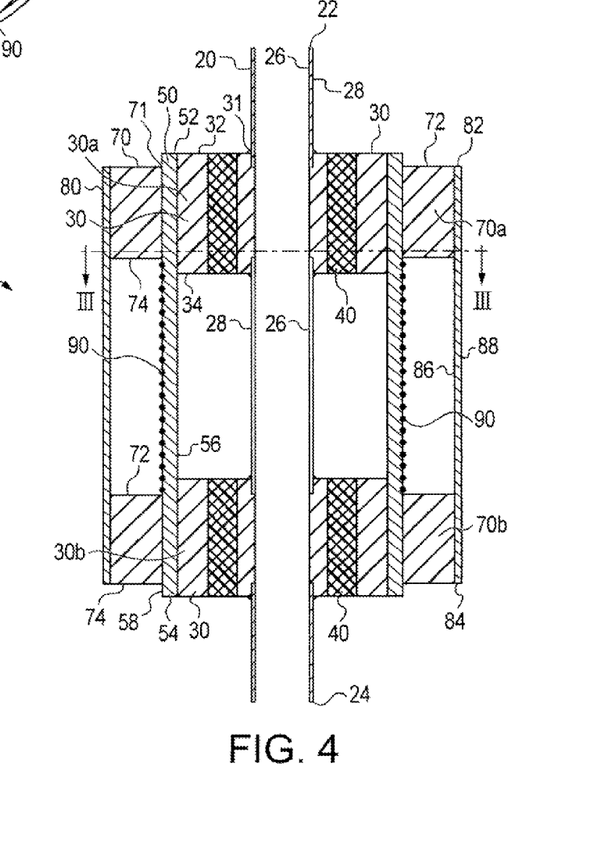
FIG. 4 is a schematic cross sectional view taken along the longitudinal axis of the preferred embodiment chromatography apparatus depicted in FIG. 3.
Figure 5:
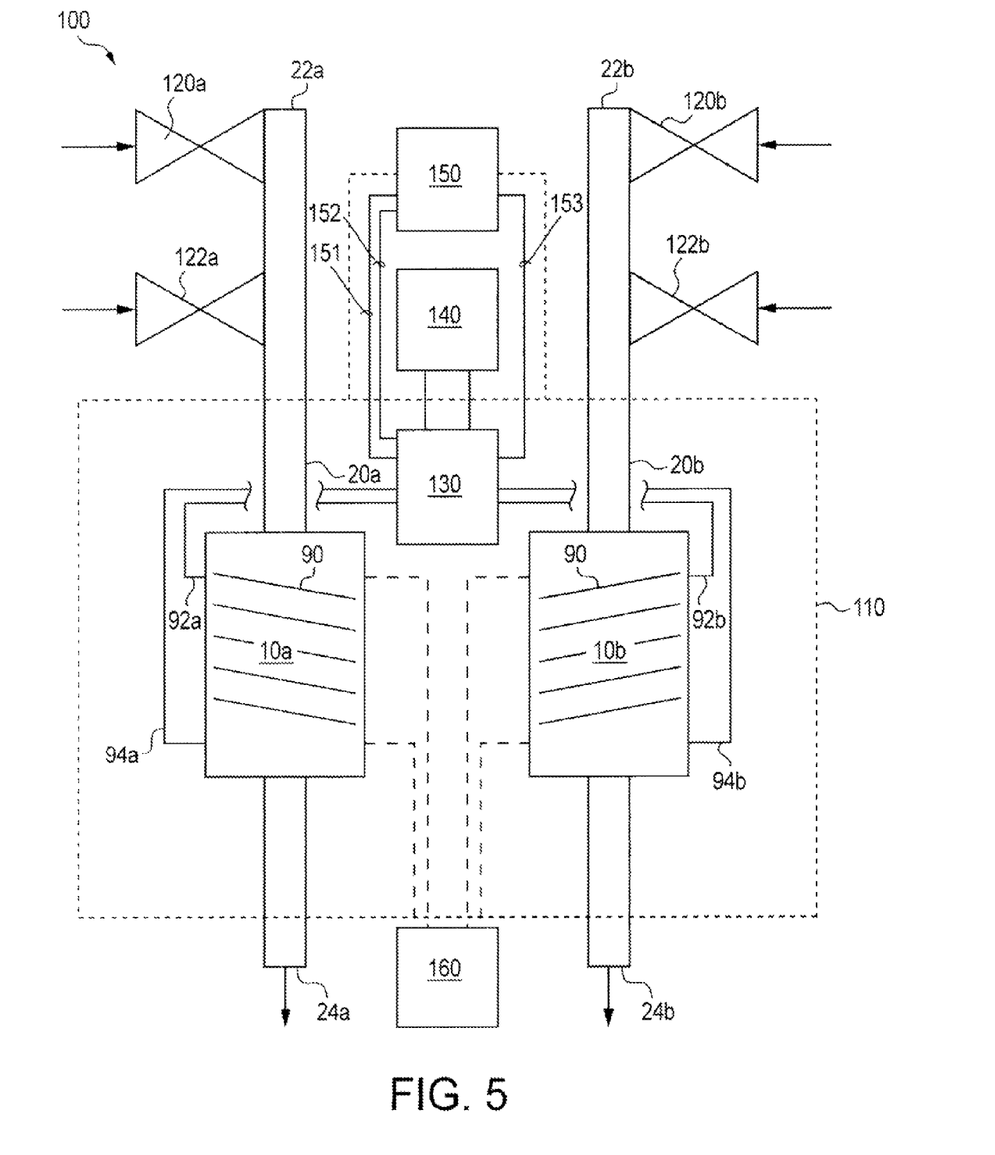
FIG. 5 is a schematic diagram of a preferred embodiment system in accordance with the present invention comprising two of the preferred apparatuses depicted in FIGS. 3 and 4.

A preferred embodiment apparatus for application of a moving temperature gradient to a capillary chromatography column in accordance with the present invention and which is used in the examples described herein is shown schematically in FIGS. 3-5. The preferred embodiment apparatus 10 is schematically shown in FIGS. 3 and 4. FIG. 3 is a schematic cross sectional view of the apparatus 10 illustrated in FIG. 4 taken along line III-III in FIG. 4. The apparatus 10 comprises one or more inner member(s) 20, an outer member 80, and a medial member 50 disposed between the inner and outer members 20 and 80. Preferably, the inner member 20, the medial member 50, and the outer member 80 are in the form of cylindrically shaped hollow members or tubes, and concentrically arranged with respect to each other such that they share a common longitudinal axis. However, it will be understood that the present invention includes a wide range of other configurations and assemblies for the apparatus 10, and specifically, the members 20, 50, and 80.

As illustrated in the longitudinal cross section of FIG. 4, it is preferred that the medial and outer members 50 and 80, respectively, extend continuously over their lengths. The inner member 20 however, may be in the form of a collection of shorter lengths, spaced apart from one another along their longitudinal axis as shown in FIG. 4. Alternately, the invention includes the inner member 20 continuously extending across the entire length of the apparatus 10.

The inner member 20 or collection of longitudinally aligned members 20, defines a first end 22 and a second opposite end 24. And, the inner member 20 defines an interior surface 26 and an oppositely directed outer surface 28. Similarly, the medial member 50 defines first and second ends 52 and 54, and inner and outer surfaces 56 and 58, respectively. Likewise, the outer member 80 defines first and second ends 82 and 84, and inner and outer surfaces 86 and 88, respectively.

The preferred apparatus 10 also comprises one or more interior heat distributor components 30, preferably positioned between the inner member 20 and the medial member 50. For the version depicted in FIGS. 3 and 4 in which the inner and medial members 20 and 50 are concentrically arranged hollow cylinders, the heat distributor component 30 can be in the form of an apertured cylinder defining a central aperture 31 sized and configured to receive the inner member 20. The heat distributor component also preferably defines a first face 32 and an oppositely directed second face 34.

Preferably, the heat distributor component 30 defines one or more hollow regions 35 that are sized and configured to receive a corresponding number of heaters 40. Preferably, the heaters 40 are electrically operated cartridge heaters as known in the art.

The apparatus 10 can comprise one, two, or more of the heat distributor components 30. In the version shown in FIGS. 3 and 4, two heat components 30 are used. These are shown as components 30a and 30b. Preferably, the number and positioning of the heat components 30 within the apparatus 10 will depend upon the length of a capillary column that extends along a portion of the medial member 50. These aspects are described in greater detail herein.

The preferred embodiment apparatus 10 also comprises an outer clamp member or clamp 70, preferably disposed between the medial member 50 and the outer member 80. For the version shown in FIGS. 3 and 4 in which the medial and outer members 50 and 80 are concentrically disposed hollow cylinders, the outer clamp member 70 can be in the form of an apertured cylinder defining a central aperture 71 sized and configured to receive the medial member 50. The outer clamp member 70 preferably defines a first face 72 and an oppositely directed second face 74. The use of multiple clamp members 70 is contemplated. In many instances, it will be preferred to use the same number of clamp members 70 as the number of heat distributor components 30 that are used. Each clamp member 70 is then preferably positioned about a corresponding heat distributor component 30, as shown in FIG. 4.

As previously noted, the heat distributor component 30 may be in the form of multiple components, spaced apart from each other as shown in FIG. 4. And, as noted, the outer clamp member 70 is preferably in the form of two such members, spaced apart from one another along the longitudinal axis of the apparatus 10. In the preferred arrangement shown in FIG. 4, an upper clamp member 70a and a lower clamp member 70b are provided.

The preferred embodiment apparatus 10 further comprises one or more capillary GC column(s) 90 preferably in contact with the medial member 50, and most preferably helically wrapped around and in thermal communication with the outer surface 58 of that member. The capillary column 90 defines a first end (not shown) and a second end (not shown). Preferably, the capillary column(s) 90 are positioned alongside the outer surface 58 of the medial member 50, between the upper clamp member 70a and the lower clamp member 70b.

Thus, referring to FIG. 4 of the preferred apparatus 10, it will be appreciated that a temperature gradient can be established along the length of the GC capillary column 90, i.e. between its first and second ends, by controlling the operation of the heaters 40 in the heat distributor components 30 positioned proximate those ends. For example, assuming a first inlet end of the GC capillary column 90 is adjacent an upper heat distributor component 30a, and a second outlet end of the GC capillary column 90 is adjacent a lower heat distributor component 30b, temperature gradients such as depicted in FIGS. 1 and 2 can be achieved by heating the temperature of the upper heat distributor component 30a to a temperature that is greater than the temperature of the lower heat distributor component 30b. It will be appreciated that such heating can be performed by selective control of the electrical heaters 40 associated with each of the components 30a and 30b.

More preferably, the GC capillary column 90 is mounted directly on the medial member 50 that serves as a temperature gradient column support as shown in FIG. 4. In this regard, the medial member 50 or column supports preferably comprise a 2 inch o.d. aluminum tube that defines a spiral groove along its exterior 58. Approximately 4 m length of GC capillary column 90, approximately 0.25 mm i.d. and containing a 0.25 μm stationary phase film thickness on its interior wall, is wound around the medial member 50 within the groove. A copper heat distributor 30 and six 150 W cartridge heaters 40 are positioned at each end of the medial member 50 and operated to a controlled temperature. The two heat distributor components 30 are connected together on axis by a 0.5 inch o.d. stainless steel tube, i.e. the inner support member 20, that can be brazed to the heat distributors. Two additional 0.5 inch o.d. stainless steel tubes, i.e. additional inner support members 20, can be brazed or otherwise attached to the outer ends of the heat distributors 30 to form a conduit through the axis of the medial member 50 for coolant (such as for example air or water) flow. The medial member 50 is preferably affixed at each end to a heat distributor 30 with a copper clamp 70. An outer aluminum tube serving as the outer support member 80 is preferably secured to the outside of the copper clamps 70 with worm-drive hose clamps (not shown). It will be understood that in no way is the present invention limited to this particular configuration.

The present invention also provides a system utilizing one, two, or a plurality of the preferred embodiment apparatus columns and supports for application of a moving temperature gradient. Referring to FIG. 5, a preferred embodiment system 100 in accordance with the present invention is depicted. The system 100 comprises a plurality of apparatuses such as previously described apparatus 10, shown in FIG. 5 as 10*a* and 10*b*. Each apparatus 10*a*, 10*b* defines a first end 22 and a second end 24. Thus, apparatus 10*a* defines a first end 22*a* and a second end 24*a*. And, the second apparatus 10*b* defines a first end 22*b* and a second end 24*b*. It will be understood that the first ends 22*a* and 22*b* correspond to the previously described end 22 of the apparatus 10 depicted in FIG. 4. And similarly, the second ends 24*a* and 24*b* correspond to the previously described end 24 of the apparatus 10. Preferably, each of the apparatuses 10*a* and 10*b* are disposed within an environmentally controlled chamber 110, such as for example a GC oven as known in the art. One or more valves are provided in flow communication with the apparatuses 10*a* and 10*b*. For example, valves 120*a* and 122*a* can be provided proximate the first end 22*a* of the apparatus 10*a*. And valves 120*b* and 122*b* can be provided proximate the first end 22*b* of the apparatus 10*b*. One or more of these valves can be used to control flow of air, water, and/or other flowable heat transfer media. Such heat transfer media is preferably used in conjunction with the previously described heaters, i.e. heaters 40, positioned at opposite ends or along desired regions of each apparatus 10*a*, 10*b*, to selectively heat and/or cool each apparatus 10*a*, 10*b* or region thereof. Details of such heating and/or cooling are described in greater detail herein.

The system 100 further comprises a multi-port valve assembly 130 as described in greater detail herein. The valve assembly 130 is preferably a two-position, ten (10) port valve assembly as known in the art. The valve assembly 130 can be controlled and/or operated by an electronic controller 140, also described in greater detail herein.

The system 100 also preferably comprises one or more detectors, shown as 150. The detector(s) 150 can include multiple detectors, and detectors of different types, and preferably includes a detector with multiple detection channels, referred to herein as channels A, B, C . . . etc. As will be appreciated by those skilled in the art, the detector includes one or more inlet ports and one or more outlet ports. The detector 150 can include a microvolume thermal conductivity detector. The detector 150 is used to detect, analyze, and/or quantify one or more analyte(s) of interest.

Referring to FIG. 5, preferably, a first or inlet end of the capillary column 90 of the apparatus 10*a* is in flow communication with the valve assembly 130 via a flow line 92*a*. And, a second or outlet end of the capillary column 90 of the apparatus 10*a* is in flow communication with valve assembly 130 via a flow line 94*a*. Similarly, a first or inlet end of the capillary column 90 of the apparatus 10*b* and a second or outlet end of the capillary column 90 of the apparatus 10*b*, are in flow communication with the valve assembly 130 via flow lines 92*b* and 94*b*, respectively.

Figure 6:
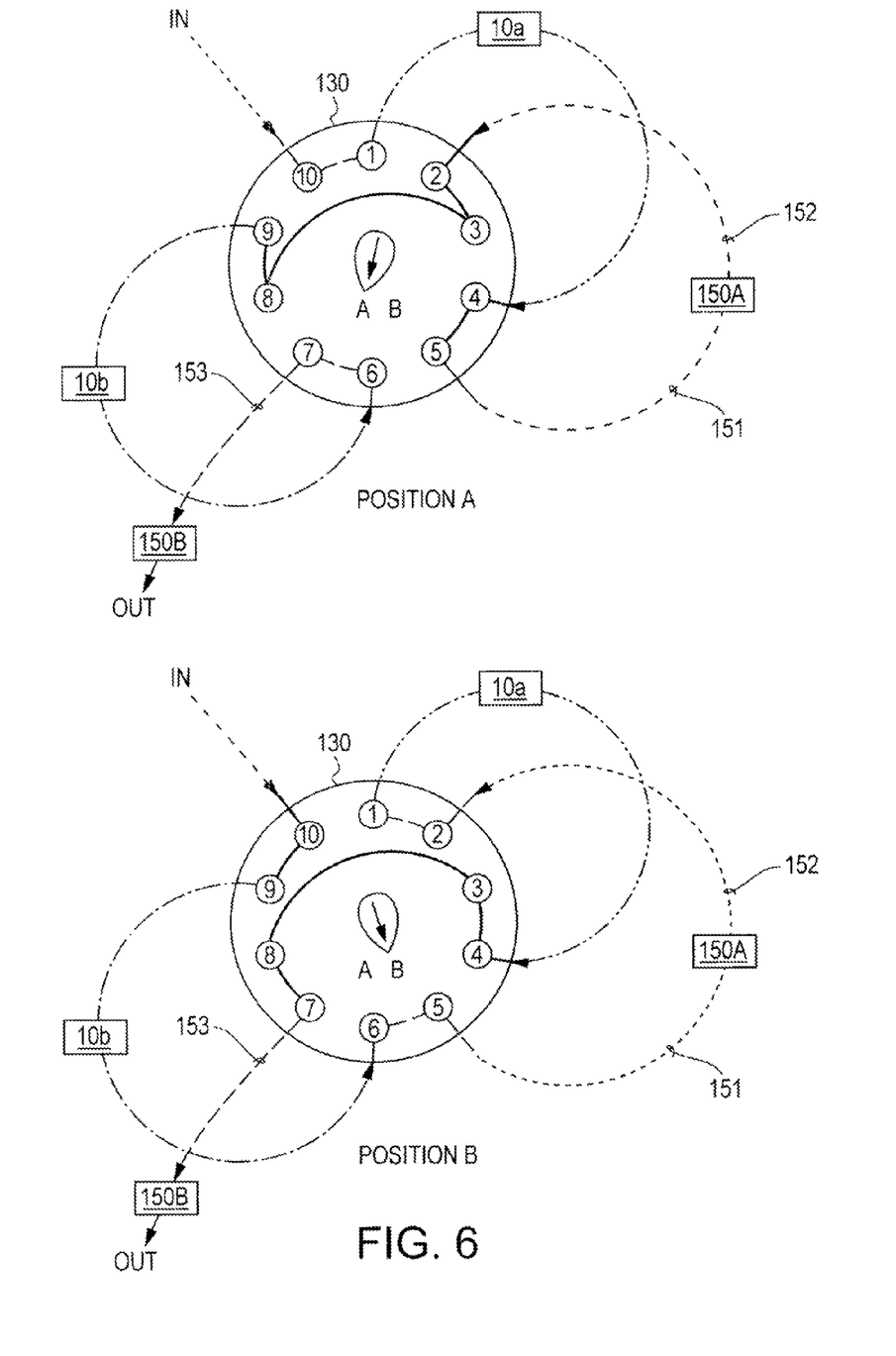
FIG. 6 is a diagram illustrating a preferred switching configuration for a switching valve used in the preferred system of FIG. 5.

Referring to FIGS. 5 and 6, detector 150 channel A inlet is in flow communication with valve assembly 130 via flow line 151. And detector 150 channel A outlet is in flow communication with valve assembly 130 via flow line 152. And detector 150 channel B inlet is in flow communication with valve assembly 130 via flow line 153. For example, detector channel A and channel B are TCD detectors. Alternatively, detector channel A is a TCD detector and channel B is a flame ionization detector or mass spectrometer.

The system 100 may also comprise one or more electronic controllers 160 as known in the art for controlling the temperatures at desired locations along each of the apparatuses 10*a* and 10*b*. Preferably, an electronic controller 160 controls the operation of heaters such as cartridge heaters 40 disposed in heat distributor components 30 positioned at inlet and outlet ends, and/or at other desired regions, of a corresponding GC capillary column 90 associated with each of the apparatuses 10*a* and 10*b*. As will be appreciated by those skilled in the art, such controllers are interfaced with the heaters by one or more control signals and one or more temperature sensors in the vicinity of the heated or cooled regions of the apparatuses 10*a* and 10*b*.

In a preferred version of the previously described system 100, two identical column support assemblies, i.e. apparatus 10*a* and 10*b*, are enclosed in a GC oven (Hewlett Packard 5890A) as shown in FIG. 5. A 2-position, 10 port GC switching valve 130 (available from Valco Instrument Co. of Houston, Tex.) is also enclosed in the GC oven. A microvolume thermal conductivity detector 150 (available from Valco) can be mounted to the top of the GC oven with inlets for both detector channels inserted into the oven through apertures formed in the GC oven enclosure. The 0.5 inch o.d. stainless steel tubes of the column support assemblies, i.e. the inner support members 20*a* and 20*b*, can be passed through the top of the GC oven and connected to electrically operated solenoid valves, i.e. the valves 120*a*, 120*b*, 122*a*, and 122*b*, for control of the coolant flow. The outlet ends of the stainless steel tubes 24*a* and 24*b* are passed through the bottom of the GC oven and connected to rubber hose (not shown) or other flow collecting means through which the coolant can be recirculated or directed to a drain.

A set of preferred connections for the preferred ten port GC switching valve 130 is shown in FIG. 6. The selection valve 130 is preferably used to switch the order or flow sequence of the two columns. In position A, the gas used for the GC mobile phase passes first through column A designated as 10*a*, then the thermal conductivity detector (TCD) channel A designated as 150A, then through column B designed as 10*b*, then through TCD channel B designated as 150B, and out. Thus, the outlet end of the column for apparatus 10*a* is in immediate flow communication with the inlet end of the column for apparatus 10*b*. The term "immediate flow communication" refers to this direct flow configuration between outlet and inlet ends of serially flow-connected columns even though one or more detectors such as detector 150 or other ancillary components are disposed therebetween. With the valve in position B, the flow of gas is first through column B shown as 10*b*, then TCD channel A shown as 150A, then through column A shown as 10*a*, then through TCD channel B shown as 150B, and out. Similarly, the outlet end of the column for apparatus 10*b* is in immediate flow communication with the inlet end of the column for apparatus 10*a*. It will be understood that the present invention includes the use of other valving and switching configurations.

Figure 7:
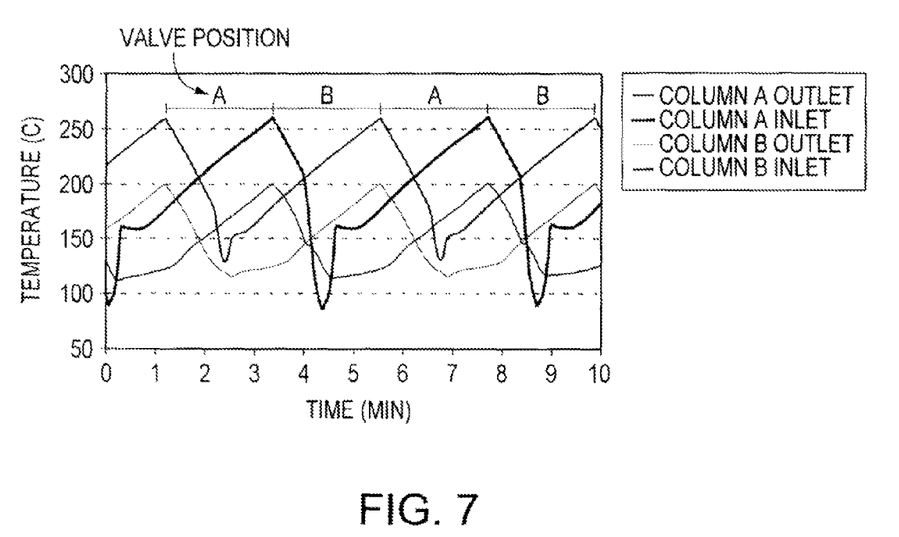
FIG. 7 is a diagram illustrating typical relationships between temperature and time as measured at four locations along the preferred apparatus of the invention.

In accordance with a preferred method of the present invention, a moving temperature wave is induced on each column support, i.e. medial member 50, by creating a temperature gradient that varies both in space (along the column support) and in time. A representative set of temperature versus time curves is shown in FIG. 7 for four (4) locations within the system at which the temperature was controlled (column A inlet, column A outlet, column B inlet, column B outlet). The columns were alternately heated and cooled. The position of the GC switching valve is also shown in the graph. When the temperature of a column is increasing, the solenoid valve controlling the flow of air through the center of that column support is open and the solenoid valve controlling the water is closed. When the column temperature is decreasing, the valves of the respective solenoids are switched to allow water to flow through the column support. The inlet end of each column is set at a higher temperature than the outlet end, and the inlet end of the second column (column B when the GC switching valve is in position A, and column A when the GC switching valve is in position B) is set to approximately the same temperature as the outlet end of the first column (column A when the GC switching valve is in position A, and column B when the GC switching valve is in position B).

The temperature difference between the column ends is preferably set so that the temperature wave speed is equal to the migration speed of the analyte(s) of interest at some temperature on the gradient. The temperature wave speed is given by equation (I) as follows:

$$U_{TW} = \frac{(\partial T / \partial t) \cdot L}{T_{inlet} - T_{outlet}} \quad (I)$$

where T is the temperature, t is time, and L is the length of the column. The migration speed of an analyte is given by equation (II) as follows:

$$U_M = \frac{F \cdot R_f(T)}{\pi \cdot r^2} \quad (II)$$

where F is the carrier gas (or mobile phase) flow rate (volume per unit time), $R_f(T)$ is the temperature-dependent analyte (or chemical species) retention factor, and r is the internal radius of the GC capillary column. When the moving temperature wave is established, each analyte focuses at the point on the wave at which $U_M = U_{TW}$. Generally, the retention factor is a decreasing function of temperature, so the more strongly retained analytes will focus at higher temperature points on the temperature wave and the more weakly retained analytes will focus at lower temperature points. The focused peaks move with the temperature wave along the first column, through the TCD channel A, and into the second column. When all of the peaks of interest are on the second column, the position of the GC switching valve is changed so that the second column becomes the first column. The focused peaks are thus circulated around the loop formed by the two columns and the TCD.

Although not wishing to be bound to any particular theory, it is believed that the matching of the temperature wave to the speed of the analyte may in many instances, occur automatically. That is, the speed of the analyte adjusts until it matches the speed of the temperature wave. Therefore, in a system and/or process in accordance with the present invention, it is necessary that the speed of the temperature wave is equal to the speed of the analyte at a temperature within the range of the applied temperature wave. If this condition is satisfied, then the analyte will adjust itself so that it is moving along at the same speed as the temperature wave.

In accordance with the present invention, a method for analyzing one or more analyte(s) from a mixture is provided. The method recirculates the analytes in a chromatography system as described herein. The system includes multiple chromatography apparatuses. Each apparatus includes a column having a stationary phase and defining inlet and outlet ends, and a heating assembly in thermal communication with the column. The apparatuses are in serial flow communication with each other to thereby define a flow loop. The method comprises introducing one or more analyte(s) into the flow loop. The method also includes operating the heating assemblies of the apparatuses such that a temperature gradient is formed over at least a portion of a corresponding column in each of the apparatuses. The heating assemblies are operated such that the temperature gradient moves along at least a portion of the corresponding column. The method also comprises continuing the operation of the system until the one or more analyte(s) are circulated about the flow loop defined by the apparatuses.

In this method, it is preferred that the heating assembly of the first apparatus is operated such that the temperature at the inlet end of the column is greater than the temperature at the outlet end of the column. It is also preferred that the heating assembly of the second apparatus is operated such that the temperature at the inlet end of the column is greater than the temperature at the outlet end of the column. Furthermore, for certain applications, it may also be preferred that the heating assembly of at least one of the first and second apparatus is operated such that the inlet end of the column of the second apparatus is approximately the same as the temperature of the outlet end of the column of the first apparatus. Generally, for most procedures, the first apparatus and the second apparatus are alternately heated and cooled with respect to each other.

The previously described method may also include removing one or more undesired chemical species from the system. Generally, this involves identifying one or more undesired analyte(s) circulating within the flow loop. And then, the method involves selectively removing the one or more undesired analyte(s) from the flow loop.

The present invention also includes a method for improving detection limits in a gas chromatography system including a first and a second apparatus. Each apparatus comprises (i) a column and a stationary phase disposed in the column, the column adapted to receive a flowing mobile phase and carrier gas, the column defining an inlet end and an outlet end, and (ii) a heating assembly in thermal communication with at least a portion of the column. The first and the second apparatuses are in flow communication with each other such that carrier gas flowing from the outlet end of the first apparatus flows to the inlet end of the second apparatus and carrier gas flowing from the outlet end of the second apparatus flows to the inlet end of the first apparatus. The method comprises introducing a sample containing one or more analyte(s) of interest into the flowing carrier gas and forming a moving temperature wave along the columns in the first and second apparatuses. Analyte(s) of interest accumulate in the carrier gas and can be detected as focused peaks.

Figure 8:
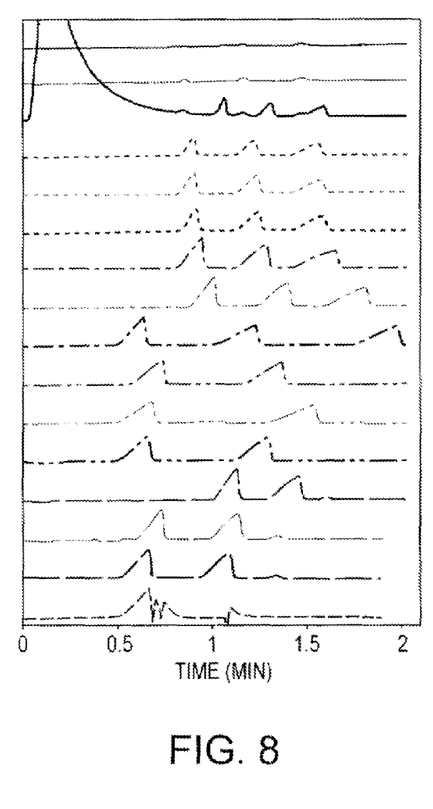
FIG. 8 is a diagram illustrating a sensor signal over time for a first valve position during a preferred method of the present invention.
Figure 9:
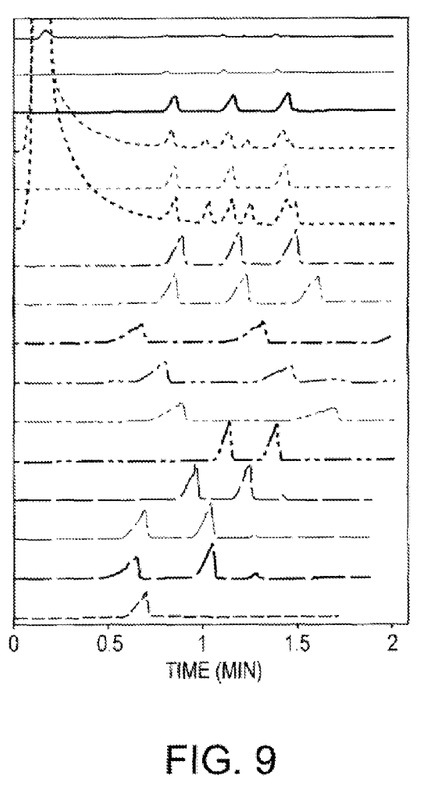
FIG. 9 is a diagram illustrating the sensor signal over time referred to in FIG. 8 for a second valve position.

An example of the TCD signal during a separation using a preferred embodiment method in accordance with the present invention is shown in FIGS. 8 and 9. For this example, the previously described system 100 and apparatus 10a and 10b (corresponding to apparatus 10) were used. The TCD temperature was set to 180° C., TCD filament A was set to 7.0, and TCD filament B was set to 5.5. The GC oven was set to 220° C., and the GC injector temperature was set to 300° C. Helium was used as the carrier gas, at a flow rate of approximately 4.1 mL/min (61 psi head pressure). The data is arranged in two graphs showing the signal when the GC switching valve was in position A (FIG. 8) and when the GC switching valve was in position B (FIG. 9), and in time from top to bottom. The three analytes used were octadecane ($C_{18}$), nonadecane ($C_{19}$), and eicosane ($C_{20}$). The sample used was 0.75% (all percentages noted herein are by weight unless indicated otherwise) $C_{18}$, 0.84% $C_{19}$, and 0.84% $C_{20}$ in decane. For the first data set (FIG. 8, top) there was already a small amount of $C_{18}$, $C_{19}$, and $C_{20}$ focused on the temperature wave from a previous injection. At the beginning of the next data set (FIG. 9, top) a small additional amount of sample was injected. The sample was injected through the HP 5890A split/splitless injector with the split vent closed (splitless mode). The peak occurring at about 0.18 minutes on the top trace of FIG. 9 is the decane peak passing quickly through the column and to the TCD. For the next data trace ($2^{nd}$ from top), it can be seen that the size of the focused $C_{18}$, $C_{19}$, and $C_{20}$ peaks is increased slightly from the injection. The $C_{10}$ peak does not continue to circulate with the temperature wave because for decane, $U_M > U_{TW}$ for all temperatures on the gradient. The decane thus quickly passes through both columns and out of the system to waste. At the beginning of the third trace (from the top) in FIG. 8, a larger injection of the same sample was made. For that trace, there were 6 analyte peaks (plus the decane peak) because the newly injected $C_{18}$, $C_{19}$, and $C_{20}$ peaks had not yet reached their steady-state positions on the temperature wave. For the next trace (third from top, in FIG. 9), the analytes had arrived at their steady state positions and there were again 3 peaks—though they were significantly larger since they contained the sum of analytes from all the previous injections. Similarly, after the large injections at the beginnings of the $4^{th}$ and $6^{th}$ trace in FIG. 9, there were initially 6 peaks, but then 3 peaks again for later traces as the analytes arrived at their steady state positions. With each injection, the analyte peaks became bigger since they contained all the analyte from the previous injections. In accordance with the present invention, this demonstrates a strategy for improving detection limits in GC to a greater degree than prior art GC methods. Specifically, repeated injections can be made (using either the direct splitless injection used here or any other prior art GC injection technique), and all of the analytes from those injections can be summed into the focused peaks.

Alternately, the analytes can be introduced into the chromatography system continuously, as a mixture with the mobile phase. In this case, the analytes would also be focused into peaks, and the end result would be similar to the summation of several discreet injections. Advantageously, the continuous introduction of sample mixed with mobile phase would occur until the analytes of interest were focused to a detectable level, and then it would be replaced by pure mobile phase to clean up the tailing due to the continuous stream of new analyte moving into the focused peaks.

Figure 10:
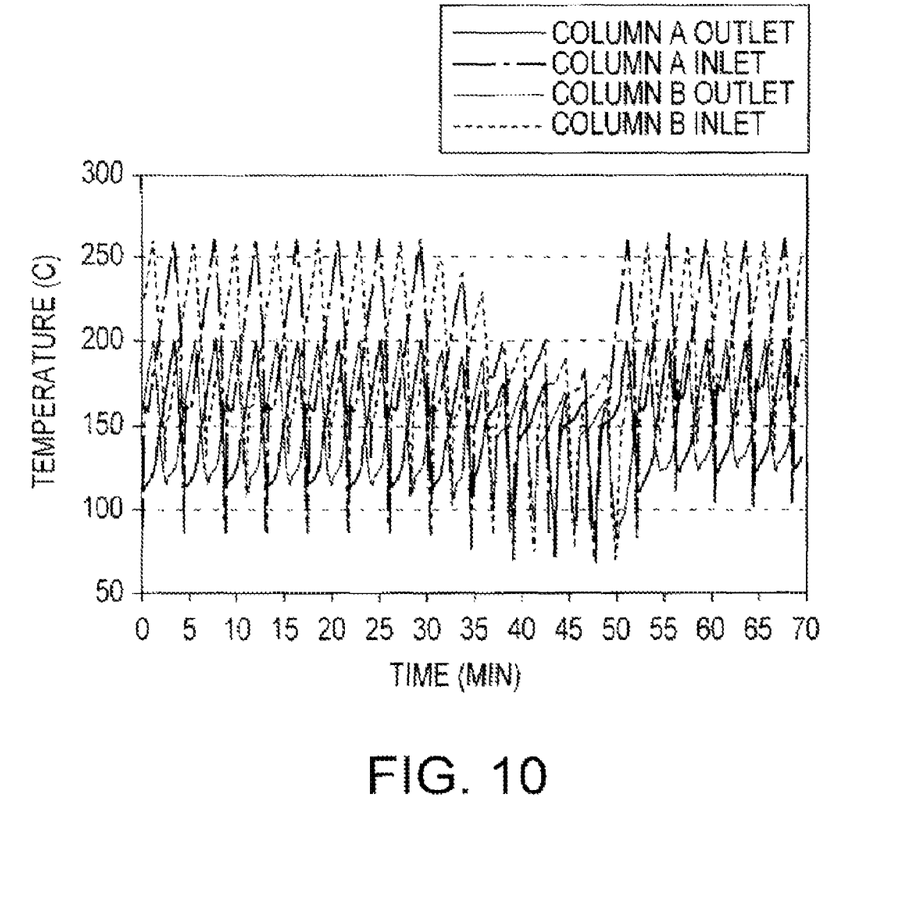
FIG. 10 is a diagram illustrating complete temperature versus time curves for all of the data presented in FIGS. 8 and 9.

FIG. 10 illustrates a plot of complete temperature versus time curves used for all of the data in FIGS. 8 and 9. Between a time of 31 min and a time of 45 min ($8^{th}$ through $12^{th}$ trace in FIG. 8, $8^{th}$-$11^{th}$ trace in FIG. 9), the temperature gradient was reduced, stretching out the peak pattern and improving the resolution. At a time of approximately 42 min ($10^{th}$ trace from the top in FIGS. 8 and 9), the gradient was reduced so that for $C_{20}$, $U_M < U_{TW}$ for every temperature on the gradient, and the $C_{20}$ peak was pushed off the end of the gradient where it was eluted from the system, and detected by TCD channel B. At a time of about 50 min, the temperature gradient was increased bringing the peak positions back together. At a time of approximately 66 min (last trace, left graph in FIG. 8), the position of the GC switching valve was changed briefly to "cut out" the $C_{19}$ peak and send it to the TCD channel B.

Figure 11:
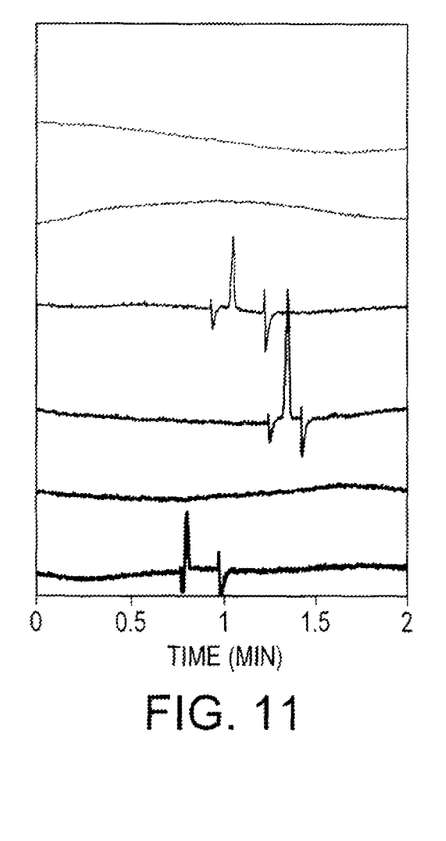
FIGS. 11-13 are diagrams illustrating selective peak cutting achieved in accordance with another aspect of the present invention.
Figure 12:
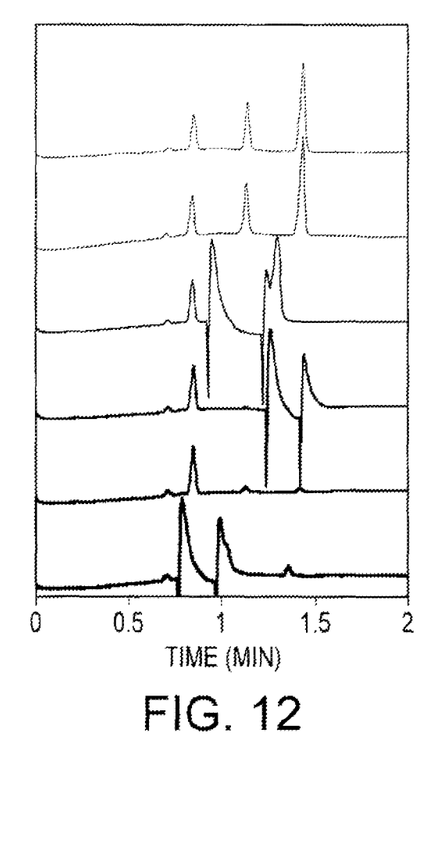
Figure 13:
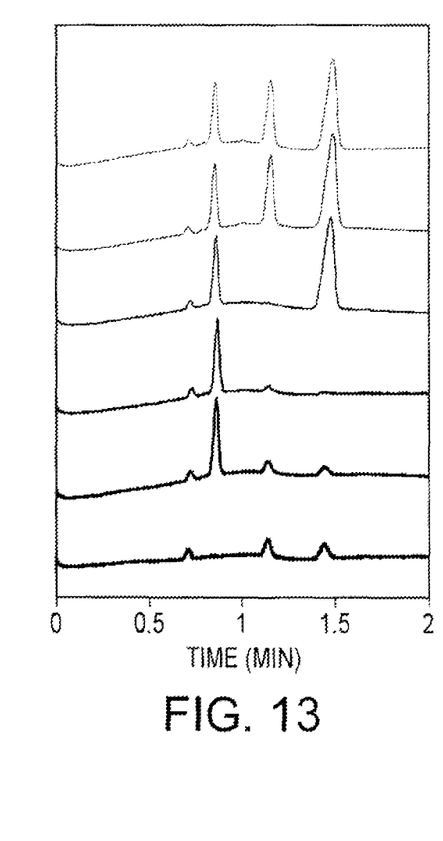

Another example of selective peak cutting is shown in FIGS. 11-13. FIG. 12 and FIG. 13 are similar to previously described FIGS. 8 and 9. FIG. 11 shows the response of the TCD channel B. The three major peaks seen in the top two traces of FIG. 12 and FIG. 13 correspond to $C_{18}$, $C_{19}$, and $C_{20}$. The small peak before the $C_{18}$ peak is an unidentified system impurity peak. The third trace in each graph shows the result of cutting out the $C_{19}$ peak. The signal from TCD channel B (FIG. 11) shows two sharp spikes where the position of the GC switching valve was changed, and the $C_{19}$ peak between the two spikes. The signal from TCD channel A (FIG. 12) shows two sharp downward spikes—again at the times where the valve position was changed. The third trace in FIG. 13 shows the peak pattern a half cycle after the peak cutting; the $C_{19}$ peak is absent. Similarly, in the $4^{th}$ trace of each of FIGS. 11-13, the $C_{20}$ peak was selectively cut out, and in the $6^{th}$ trace, the $C_{18}$ peak was cut out. After being cut out, the peaks slowly increased in intensity because of residual sample bleeding out of the injector.

Thus, in accordance with the present invention, and in particular, in accordance with a preferred method in which a carrier gas is flowed about a loop defined between two or more columns, as in system 100 previously described herein, one or more undesired analyte(s) or chemical species can be selectively removed from the flowing gas. This practice is referred to herein as selective removal or peak cutting.

The examples described herein illustrate the versatility of the present invention and the capabilities that it provides that are not provided by any prior art chromatographic method. Specifically, these features include the ability to maintain a pattern of separated peaks as they circulate around a multicolumn loop and particularly a two column loop; an ability to manipulate a peak pattern to change the resolution of a separation; and an ability to selectively remove peaks from one or more peak patterns, such as may then be sent to a second detector. These abilities allow a user to selectively preconcentrate a trace analyte even if the analyte is in a sample containing high concentrations of other analytes that have similar retention characteristics as the trace analyte of interest. For example, note that the unknown trace impurity peak in FIGS. 11-13 was unaffected when the nearby $C_{18}$ peak was cut out. A possible procedure for this would be to use multiple injections, and after one or more injections cut out the high concentration analyte peaks, leaving the trace analytes to accumulate until they reach a detectable level.

Additional real-time control of the separation could be provided if more independent temperature control points were added along each column support. With additional temperature control points, it would be possible to more freely control the shape of the applied temperature gradient. Gradients that are linear, piece-wise linear, non-linear, monotonic, or non-monotonic could be applied to achieve particular desired results. For example, a piece-wise linear or nonlinear gradient could be applied to "stretch out" and improve the resolution of portions of a chromatogram without pushing other analyte peaks off the end of the gradient; or a non-monotonic gradient could be used to split a single analyte into multiple peaks or to analyze multiple samples on the same gradient.

Although the examples described herein were implemented with GC capillary columns, the retention factor is temperature dependent for every mode of chromatography and for every type of chromatographic column. Consequently, the present invention could be implemented in a similar manner with other modes of column chromatography such as for example, high performance liquid chromatography (HPLC), supercritical fluid chromatography (SFC), etc., and with other types of columns such as for example, packed columns or micro packed columns instead of capillaries. The present invention may also be implemented with spatial velocity gradients generated with means other than temperature gradients, such as with mobile phase composition gradients in HPLC, or pressure gradients in SFC, for example.

The present invention can also be implemented with one gradient column and one delay column. In this case, the analyte peaks would be focused on the gradient column while the column temperature is increasing as in the previously noted examples, and then they would be eluted into the delay column which would serve to contain the peak pattern while the gradient column was cooling back down to start the cycle again. The delay column would preferentially have a low retention for the analytes so that the relative positions of the peaks would not be changed as they move through the delay column. For example, a deactivated fused silica capillary or other tubing with similar inner diameter as the gradient column and with low analyte retention could be used as the delay column. An additional way to assure low retention on the delay column would be to maintain the gradient column at a uniform and constant temperature at which the retention is very low. Preferably, in this scenario, the delay column has a retention that is relatively low for one or more analytes of interest and is substantially constant in time and substantially uniform along the length of the delay column.

Also, more than two gradient columns could be used advantageously if, for example, a long time is required to cool each gradient column back to a low temperature after the focused peaks have eluted from the column to the next column in the series.

In addition, the present invention could be implemented using planar, chip-based chromatography columns as described in Terry, Jerman, and Angell, *IEEE Transactions on Electron Devices*, vol. 26, pp. 1880-1886, 1979. In this case, a zig-zag separation channel pattern could be used in place of the spiral capillary column described in the examples herein.

Additional Chromatography Modes

The present invention, could, in principle, be performed for any mode of chromatography where the analyte velocity is dependent on temperature. The present invention is probably best with column chromatography—since the column would be needed to contain evaporating solvents and analytes at elevated temperatures, and also to control the transfer of analytes from column to column as it goes around the loop.

For column chromatography, the different techniques can be distinguished by the type of fluid used for the mobile phase. Gas chromatography uses a gas for a mobile phase, liquid chromatography a liquid, and supercritical fluid chromatography uses a supercritical fluid. For gas chromatography and supercritical fluid chromatography, the analyte retentions and velocities are strongly temperature dependent, and so this invention could be directly implemented using a moving temperature gradient as described in the examples above. A difference between gas chromatography and supercritical fluid chromatography is that while the retention is nearly always a decreasing function of temperature for gas chromatography, it can, in many cases, be an increasing function of temperature for supercritical fluid chromatography. Consequently, this invention could be implemented with supercritical fluid chromatography either with a decreasing temperature gradient (column outlet at lower temperature than column inlet) or with an increasing temperature gradient (column outlet at higher temperature than column inlet). In addition, with supercritical fluid chromatography, the retention is typically also a strong function of the pressure. Consequently, this invention could be implemented with supercritical fluid chromatography using pressure gradients applied in both time and distance in place of the temperature gradients used in the examples described above.

When implemented with various modes of chromatography, this invention could be used with a wide variety of chromatography columns including porous-layer open-tubular (PLOT) chromatography columns, retention gap columns, and bonded phase chromatography columns, capillary columns, packed columns, micro packed columns, chiral selective columns, affinity chromatography columns, ion exchange chromatography columns, reverse phase chromatography columns, normal phase chromatography columns, size exclusion chromatography columns, and combinations thereof.

There are many different types of liquid chromatography, including affinity chromatography, ion exchange chromatography, reverse phase chromatography, normal phase liquid chromatography, and size exclusion chromatography. In general, the analyte retention velocity will always be temperature dependent to some degree, and so the invention could be applied to liquid chromatography as well, particularly with small diameter, capillary liquid chromatography columns. For an example of the effect of column temperature with liquid chromatography, see Binghe Gu et al., Analytical Chemistry, vol. 81, pp. 1488-1495 (2009). As with supercritical fluid chromatography, with liquid chromatography, the dependence of retention on the temperature can be either increasing or decreasing.

When applied with size exclusion chromatography, the present invention would be very effective in combination with a temperature-responsive size exclusion media. See for example, Lakhiari et al. "Temperature-responsive size-exclusion chromatography using poly(N-isopropylacrylamide) grafted silica," *Biochimica et biophysics acta*, vol. 1379, pp 303-313 (1998); Kanazawa and Matsushima, "Temperature-responsive chromatography," *TrAC Trends in Analytical Chemistry*, vol. 17, pp 435-440 (1998); Hosoya et al. "Temperature-Controlled High-Performance Liquid Chromatography Using A Uniformly Sized Temperature-Responsive Polymer-Based Packing Material," *Analytical Chemistry*, vol. 67, pp. 1907-1911 (1995).

Simulated moving bed (SMB) chromatography is another style of column chromatography that can be applied with either gas, liquid, or supercritical fluid as the mobile phase. As with the present invention, SMB uses a "loop" of columns and valves that switch open and closed in a pattern that rotates around the loop. There has been some work on various "gradient" modes of SMB chromatography, including a "temperature gradient" mode. See for example, Migliorini et al. "Temperature Gradient Operation of a Simulated Moving Bed Unit" Industrial & Engineering Chemistry Research, vol. 40, pp. 2606-2617 (2001). This may appear similar, in some ways, to the present invention, as it involves the use of a loop of columns that are heated and cooled as the components to be separated are moved around the loop. However, significant differences exist between gradient mode SMB chromatography and the present invention such as for example: In the temperature gradient SMB work, the different columns in the loop are at different temperatures, but the temperature of each column in the loop is spatially uniform. In the present invention there is a spatial temperature gradient applied along the length of each column in the loop. This is important because it is the temperature gradient along the length of each column that causes the analytes to focus into resolved peaks. So with the present invention, a continuous sample feed (or multiple injections) can be put into the loop where it becomes focused into multiple peaks. With SMB, a continuous stream of sample is put in, and two continuous streams are taken out—there is no focusing of analytes into peaks. Consequently, SMB is generally only useful for binary (two component) separations and purifications, and not for the analysis of complex sample mixtures.

Gradient SMB methods improve upon non-gradient SMB in that they can potentially increase the purity and concentration of the output streams and/or reduce the solvent consumption for the process. However, gradient SMB as known in the prior art is not capable of handling complex (multi-component) samples.

Many other benefits will no doubt become apparent from future application and development of this technology.

All patents, published applications, and articles noted herein are hereby incorporated by reference in their entirety.

As described hereinabove, the present invention solves many problems associated with previous type devices and methods. However, it will be appreciated that various changes in the details, materials and arrangements of parts, steps or operations of the methods which have been herein described and illustrated in order to explain the nature of the invention, may be made by those skilled in the art without departing from the principle and scope of the invention, as expressed in the appended claims.

What is claimed is:

1. A chromatography system for separating one or more analytes from a mixture, the system comprising:
    a plurality of chromatography columns, each chromatography column defining inlet and outlet ends;
    a system for generating a retention gradient in both time and distance along at least a portion of the length of at least one of said chromatography columns wherein said system for generating a retention gradient includes components for generating a temperature gradient in both time and distance along at least a portion of the length of at least one of said chromatography columns; and
    at least one selection valve in flow communication with said inlet ends and said outlet ends of the plurality of chromatography columns;
    wherein a mobile phase can be directed to flow sequentially through each of the chromatography columns, and
    wherein the at least one selection valve can be switched to control the order in which the mobile phase flows through each of the chromatography columns.

2. The chromatography system of claim 1, wherein one of the chromatography columns is a delay column, said delay column having a retention that is relatively low for the one or more analytes and is substantially constant in time and substantially uniform along the length of said delay column.

3. The chromatography system of claim 1, further comprising:
    a detector adapted to detect the presence of an analyte of interest, the detector including a first channel inlet port and a first channel outlet port,
    wherein the first channel inlet port is in flow communication with the outlet end of one of the columns, and
    wherein the first channel outlet port is in flow communication with the at least one selection valve.

4. The chromatography system of claim 1, further comprising:
    a detector adapted to detect the presence of an analyte of interest, the detector including a first channel inlet port and a first channel outlet port,
    wherein the first channel inlet port is in flow communication with the at least one selection valve, and
    wherein the first channel outlet port is in flow communication with the inlet end of one of the columns.

5. The chromatography system of claim 1, further comprising:
    a detector adapted to detect the presence of an analyte of interest, the detector including a first channel inlet port and a first channel outlet port,
    wherein the first channel inlet port and the first channel outlet port are in flow communication with the at least one selection valve.

6. The chromatography system of claim 1, wherein said components for generating a temperature gradient comprise at least one column support assembly, each column support assembly comprising:
    a support member defining a first end and a second end opposite from the first end, said support member being in thermal contact with at least a portion of one of the chromatography columns; and
    a heating assembly providing a first heating unit proximate the first end of the support member and a second heating unit proximate the second end of the support member, each of the first and second heating units being independently controllable so as to form a temperature gradient between the first and second ends of the support member and thereby to form a temperature gradient along at least a portion of the length of one of the chromatography columns.

7. The chromatography system of claim 1, wherein said components for generating a temperature gradient comprise at least one column gradient assembly, each column gradient assembly comprising:
    a conduit for a heat exchange fluid, at least a portion of one of the chromatography columns being disposed within said conduit;
    a heater disposed within said conduit in thermal transfer relation with the heat exchange fluid and with at least a portion of one of the chromatography columns; and
    a transfer system for flowing the heat exchange fluid through the conduit;
    whereby a temperature gradient is formed along at least a portion of the length of one of the chromatography columns.

8. The chromatography system of claim 1,
    wherein the chromatography system is selected from the group consisting of a liquid chromatography system, a gas chromatography system, and a supercritical fluid chromatography system, and
    wherein the chromatography columns are selected from the group consisting of packed columns, micro packed columns, capillary columns, chiral selective columns, affinity chromatography columns, ion exchange chromatography columns, reverse phase chromatography columns, normal phase chromatography columns, size exclusion chromatography columns, porous-layer open-tubular chromatography columns, retention gap columns, bonded phase chromatography columns, and combinations thereof.

* * * * *